United States Patent [19]

Staerzl

[11] Patent Number: 4,761,992
[45] Date of Patent: Aug. 9, 1988

[54] KNOCK DETECTION CIRCUIT WITH GATED AUTOMATIC GAIN CONTROL

[75] Inventor: Richard E. Staerzl, Fond du Lac, Wis.

[73] Assignee: Brunswick Corporation, Skokie, Ill.

[21] Appl. No.: 59,792

[22] Filed: Jun. 9, 1987

[51] Int. Cl.⁴ .................................... G01L 23/22
[52] U.S. Cl. ........................................... 73/35
[58] Field of Search .................... 73/35; 123/425, 435

[56] References Cited

U.S. PATENT DOCUMENTS

| | | | |
|---|---|---|---|
| 3,749,070 | 7/1973 | Oishi et al. | 123/117 R |
| 3,931,808 | 1/1976 | Rachel | 123/32 EA |
| 4,114,570 | 9/1978 | Marchak et al. | 123/23 EG |
| 4,184,560 | 1/1980 | Harada et al. | 123/32 EG |
| 4,243,009 | 1/1981 | Staerzl | 123/435 |
| 4,312,214 | 1/1982 | Kramer et al. | 73/35 |
| 4,312,314 | 1/1982 | McChesney et al. | 123/438 |
| 4,349,000 | 9/1982 | Staerzl | 123/491 |
| 4,391,254 | 7/1983 | Staerzl | 123/478 |
| 4,429,673 | 2/1984 | Staerzl | 123/491 |
| 4,478,068 | 10/1984 | Bonitz et al. | 73/35 |
| 4,481,924 | 12/1984 | Kobayashi | 123/425 |
| 4,498,434 | 2/1985 | Baltz et al. | 123/187.5 R |
| 4,521,769 | 6/1985 | Dudeck et al. | 340/635 |
| 4,528,955 | 7/1985 | Sugiura | 123/425 |
| 4,621,602 | 11/1986 | Furuyama | 123/425 |
| 4,664,083 | 5/1987 | Nix et al. | 123/425 |
| 4,667,637 | 5/1987 | Staerzl | 123/435 |

FOREIGN PATENT DOCUMENTS 0199919  12/1982  Japan ........................ 73/35

Primary Examiner—Jerry W. Myracle
Assistant Examiner—Robert P. Bell
Attorney, Agent, or Firm—Andrus, Sceales, Starke & Sawall

[57] ABSTRACT

A knock detection circuit includes an audio transducer (2) converting audio signals indicative of engine combustion into output signal voltage including a portion representing background noise and a portion representing detonation. An active variable resistor is provided by a transistor (14) having a gain which adjusts the amplitude of the transducer output voltage. A sampling and controlling circuit (30, 22, 28) samples the portion of the transducer output voltage representing background noise and outputs a variable bias determined by sensed background noise, which bias controls the gain of the transistor to adjust transducer output voltage inversely with sensed background noise. A detonation threshold detector (58) responds to a predetermined increase in the amplitude of the portion of the transducer output voltage representing detonation above the amplitude of the portion of transducer output voltage representing background noise, and outputs a knock-detected signal. Gated automatic gain control self-adapts and compensates for differing transducer sensitivities providing differing sensed background noise.

16 Claims, 1 Drawing Sheet

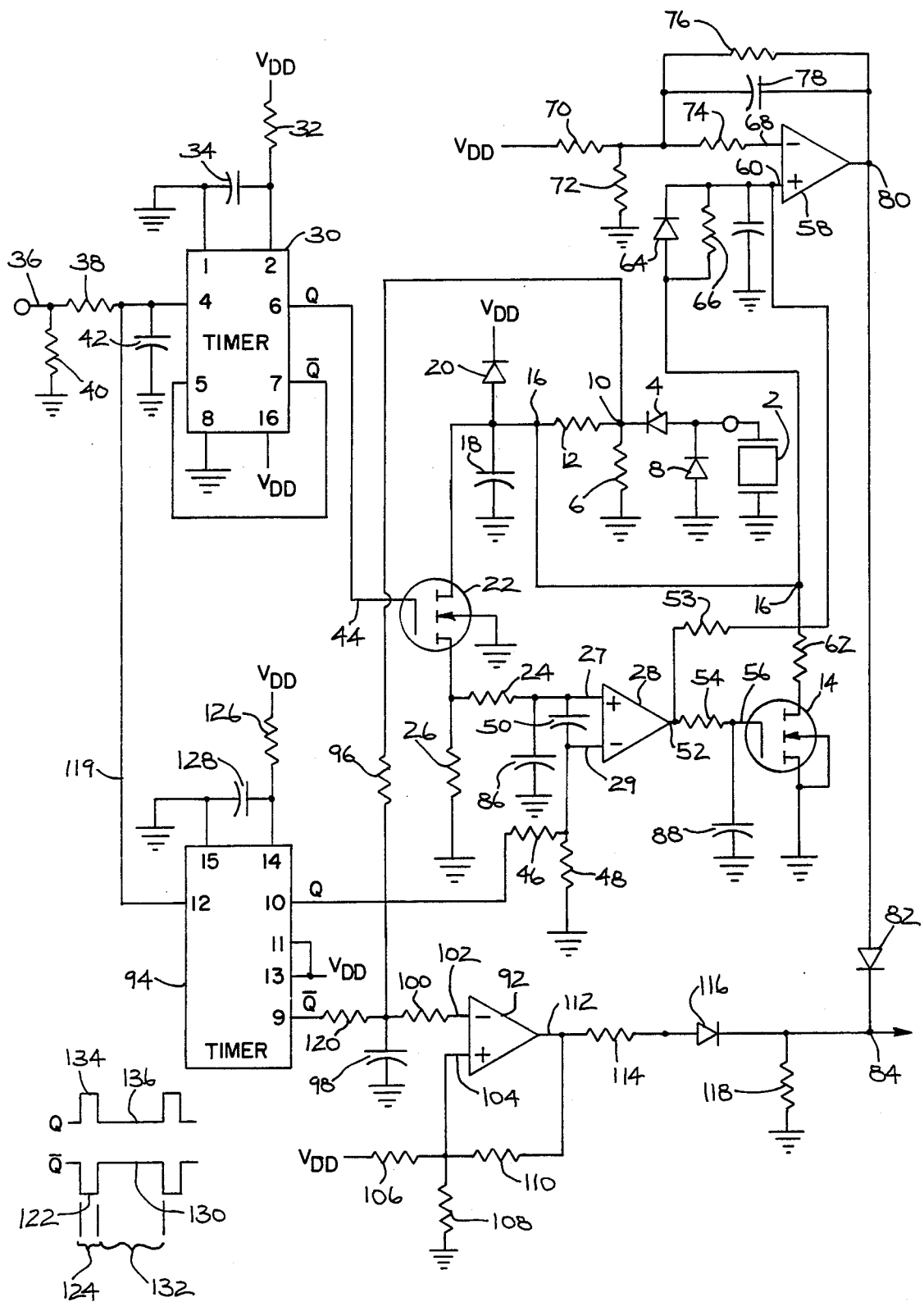

KNOCK DETECTION CIRCUIT WITH GATED AUTOMATIC GAIN CONTROL

CROSS REFERENCE TO RELATED APPLICATIONS

Reference is made to commonly owned copending U.S. application Ser. No. 60,078, filed on even date herewith and U.S. application Ser. No. 59,791, filed on even date herewith.

BACKGROUND AND SUMMARY

The invention relates to knock detection circuitry for a two cycle internal combustion engine.

Premature firing of the fuel-air mixture in the combustion chamber of an internal combustion engine causes the mixture to explode rather than burn smoothly. This phenomena is called knock or detonation, and results in loss of power and possible engine damage. Knock becomes more severe with lower fuel octane rating.

It is known in the art to sense knock with an audio transducer mounted to the engine, and to reduce knock by supplying a richer fuel-air mixture and/or adjusting spark timing, U.S. Pat. Nos. 4,243,009 and 4,667,637, incorporated herein by reference.

The present invention provides further improvements in the knock detection circuitry. Gated automatic gain control is provided for the knock transducer output voltage to vary same inversely with sensed background noise. Prior systems require a precise output from the knock transducer, and have a small tolerance deviation range. This in turn required precision transducers, and precision connection to the engine, including an exact torque specification. The present invention eliminates these precision requirements and self-adapts to varying knock transducer sensitivities.

BRIEF DESCRIPTION OF THE DRAWING

The sole drawing is a circuit diagram showing a knock detection circuit in accordance with the invention.

DETAILED DESCRIPTION

The knock detection circuit includes an audio transducer 2, for example as commercially available from Telex Corporation, formerly Turner Microphone, of Minneapolis, Minn., mounted to the cylinder head of the cylinder most prone to knocking in a multiple cylinder two cycle internal combustion engine, such as shown in U.S. Pat. No. 4,349,000, and as in the above noted patents. As in incorporated U.S. Pat. No. 4,667,637, the audio transducer is preferably tuned to the mechanical resonant frequency of the cylinder to enhance the efficiency of the transducer. Audio transducer 2 senses audio signals indicative of engine combustion and occurring within the combustion chamber of the engine and converts the audio signals into an electrical output voltage including a portion representing background noise and a portion representing detonation.

As noted in incorporated U.S. Pat. No. 4,667,637 for each engine cycle, the transducer output signal voltage is characterized by one phase during which detonation is unlikely to occur and by another phase during which any detonation is likely to occur. Immediately following the ignition signal for the respective cylinder, there is a dead-time interval of approximately 1 or 1.5 milliseconds during which detonation is unlikely to occur. During this interval, there is a buildup of pressure and heat, but usually no detonation, and hence transducer 2 only senses background noise during such interval. Following this first interval, there is a second interval which lasts until the next ignition pulse. Detonation, if any, is likely to occur during the second interval. In the present invention, the first interval is used for sampling sensed background noise and adjusting transducer output voltage.

Transducer 2 has an AC output which is rectified through diode 4 having a ground reference resistor 6. The other half cycle is conducted through diode 8. The rectified transducer output voltage at node 10 is fed through a voltage divider network provided by resistor 12 and FET 14 to provide a transducer output voltage at node 16 which varies according to conduction of FET 14. The more conductive FET 14, the more current it conducts to ground, and the lesser the voltage at node 16. Conversely, if FET 14 becomes less conductive, it conducts less current to ground, and the voltage at node 16 rises. In this manner, the amplitude of the transducer output voltage at node 16 is adjusted.

The transducer output voltage at node 16 is filtered by capacitor 18. Diode 20 to voltage reference $V_{DD}$ provides overshoot protection to protect the solid state chips in the circuit. The transducer output voltage from node 16 is then applied through FET 22 and reduced by the voltage divider network provided by resistors 24 and 26 and applied to the noninverting input 27 of comparator 28, provided by an operational amplifier. Conduction of FET 22 is controlled by a monostable multivibrator timer 30, provided by a CD 4538 timer with manufacturer-assigned pin numbers shown. Timer 30 has a one millisecond timing interval set by the RC timing circuit provided by resistor 32 and capacitor 34. The ignition pulse signal voltage on line 36 is reduced by the voltage divider network provided by resistors 38 and 40 and filtered by capacitor 42 and applied to timer 30. In response to such ignition pulse, the Q output of timer 30 goes high for one millisecond, and then goes low until the next ignition pulse.

The Q output of timer 30 is connected to control terminal 44 of FET 22 and biases the latter into conduction for the noted one millisecond interval, which provides the above noted first phase or timing interval for dead-time sampling of sensed background noise. During this interval, transducer output voltage from node 16 is applied through conductive FET 22 to the noninverting input 27 of comparator 28 for comparison against a reference voltage at the comparator's inverting input 29 supplied from a voltage source provided by the Q output of timer 94, to be described, through the voltage divider network provided by resistors 46 and 48. Capacitor 50 provides filtering between the inverting and noninverting comparator inputs. The higher the voltage amplitude at comparator input 27 relative to comparator input 29, the higher the voltage amplitude at comparator output 52. The comparator output voltage is supplied through resistor 54 to control terminal 56 of FET 14 to bias the latter into conduction, the higher the bias the more the conduction.

In operation during the noted initial one milisecond interval following an ignition pulse, an increase in sensed background noise will cause a higher amplitude transducer output voltage at node 16, which is applied through conductive FET 22 to comparator input 27, which in turn increases the bias at comparator output 52 applied to FET control terminal 56, which in turn increases conduction of FET 14, which in turn lowers the transducer output voltage at node 16 through resistor 62. Conversely, a reduction in sensed background noise provides a reduced amplitude transducer output voltage at node 16, which is applied through conductive FET 22 to comparator input 27, which in turn reduces the comparator output bias at output 52 applied to control terminal 56, which in turn reduces conduction of FET 14, which in turn increases transducer output voltage at node 16. This automatic control of the gain of FET 14 provides conduction modulation according to sensed background noise, which in turn affects the transducer output voltage at node 16. This self-adaptation is provided by transistor 14 in the feedback loop to comparator input 27. The automatic gain control is gated by timer 30 and FET 22.

A detonation threshold detector includes operational amplifier 58 having its noninverting input 60 connected to node 16 through resistor 66 and parallel diode 64. The inverting input 68 of comparator 58 is supplied with a reference voltage from voltage source $V_{DD}$ reduced by the voltage divider network provided by resistors 70 and 72 and supplied through resistor 74. the gain of op amp 58 is set by the feedback loop including resistors 76, 70 and 72, and filtering is provided by capacitor 78. When the voltage at op amp 60 rises above that at op amp input 68, the op amp output 80 goes high, which high signal is supplied through diode 82 to output 84 providing a knock-detected signal for fuel enrichment and/or spark timing adjustment, as noted in said incorporated patents.

As above noted, during the one millisecond initial timing interval, the circuit self-adapts to varying sensed background noise and provides gated automatic gain control to vary the transducer output voltage at node 16. During this interval, capacitor 86 at comparator input 27 charges. At the end of the one millisecond background noise sampling interval, the Q output of timer 30 goes low which turns off transistor 22. Charged capacitor 86 maintains voltage at comparator input 27 upon termination of such interval, in order to maintain the state at comparator output 52. Capacitor 88 at transistor control terminal 56 likewise has previously been charged during the initial interval, and upon termination of such interval will maintain a bias on control terminal 56 to maintain FET 14 conductive, to in turn maintain approximately the same resistance value across the main terminals of FET 14 between node 16 and ground. Capacitors 86 and 88 maintain a relatively smooth DC bias on respective terminals 27 and 56 at the end of the initial sampling interval to maintain the gain of transistor 14 until the next ignition pulse. The next ignition pulse will occur in about 2-2.5 milliseconds depending on engine speed.

Detonation threshold detector 58 responds to a predetermined increase in the amplitude of the transducer output voltage at node 16 above the amplitude representing sensed background noise, and ouputs the knock-detected signal at output 84. During the initial timing interval, capacitor 90 at op amp input 60 charges from node 16 through resistor 66 and diode 64. Capacitor 90 also charges through resistor 53 from output 52 of comparator 28, to provide a higher charge on capacitor 90 for higher sensed background noise. During the initial timing interval, the voltage across capacitor 90 is not sufficient to trigger threshold detector 58. At the end of the initial one millisecond timing interval, capacitor 90 maintains a bias at comparator input 60. When detonation occurs, there is a substantial increase in the voltage at node 16. Detonation threshold detector 58 responds to the increase in the amplitude of the portion of the transducer output voltage representing detonation above the amplitude of the portion of the transducer output voltage representing sensed background noise, and outputs the noted knock-detected signal.

Fail-safe and idle override circuitry includes comparator 92 and monostable multivibrator timer 94, provided by a CD 4538 timer with manufacturer-assigned pin numbers shown. Comparator 92 responds to loss of transducer output voltage at node 10 to provide a knock-detected signal at output 84 in a fail-safe mode. Timer 94 responds to engine speed below a given or idle speed to prevent the fail-safe mode even if a low amplitude transducer output voltage, corresponding to low amplitude audio signals at idle, appears to be a loss of transducer output voltage.

Transducer output voltage at node 10 is supplied through resistor 96, filtered by capacitor 98 and supplied through resistor 100 to inverting input terminal 102 of comparator 92, provided by an operational amplifier. The noninverting input 104 of comparator 92 is supplied with a reference voltage from source $V_{DD}$ reduced by the voltage divider network provided by resistors 106 and 108. Resistor 110 is connected between comparator output 112 and input 104. Comparator output 112 is connected through resistor 114 and diode 116 and protective ground resistor 118 to output 84. During normal operation, transducer output voltage at node 10 biases comparator input 102 higher than input 104, such that comparator output 112 is low, and hence there is no knock-detected signal at output 84. Upon loss of the transducer output voltage at node 10, e.g. by a failure of transducer 2, or a loose connection, etc., the voltage at comparator input 102 drops below the voltage at comparator input 104, and comparator output 112 goes high, which in turn provides a knock-detected signal at output 84. This provides a fail-safe mode.

Timer 94 provides an idle override feature. The ignition pulse from line 36 through resistor 38 is applied at line 119 to timer 94. The $\overline{Q}$ output of timer 94 is connected through resistors 120 and 100 to comparator input 102. Timer 94 responds to ignition pulses and outputs timing pulses at its $\overline{Q}$ output including a negative polarity pulse 122 for a given interval 124 set by the RC timing circuit provided by resistor 126 and capacitor 128, followed by a positive polarity pulse 130 for the interval 132 until the next ignition pulse. At low engine speed, there is sufficient duration of positive polarity pulse 130 to maintain the voltage at comparator input 102 above that at comparator input 104. This disables comparator 92 from generating a knock-detected signal at output 84 regardless of a decrease in transducer output voltage at node 10 which would otherwise decrease the voltage at comparator input 102 below that at comparator input 104.

With increasing engine speed above idle or above some given value, the duration of positive polarity pulses 130 becomes shorter because the next ignition pulses occur sooner. There is then insufficient duration of positive polarity pulses 130 to maintain the voltage at comparator input 102 above that at input 104, and hence comparator 92 is controlled by the transducer output voltage at node 10 supplied to comparator input 102, and comparator 92 generates a knock-detected signal at output 84 when the voltage at input 102 drops below that at input 104.

The fail-safe and idle override circuitry responds to loss of transducer output voltage at node 10 to provide the knock-detected signal at output 84 in a fail-safe mode. The circuitry responds to engine speed below a given speed and prevents the fail-safe mode even if a low amplitude transducer output voltage at node 10, corresponding to low amplitude audio signals at idle, appears to be a loss of transducer output voltage. At engine speeds above idle, input 102 of comparator 92 is controlled solely by the transducer output voltage at node 10 through resistor 96.

Timer 94 outputs timing pulses at its Q output including a positive polarity pulse 134 for the noted given interval 124, followed by a negative polarity pulse 136 for the noted interval 132 until the next ignition pulse. With increasing engine speed, the duration of negative polarity pulses 136 becomes shorter because the next ignition pulses occur sooner, and hence there is increasing voltage at inverting input 29 of comparator 28. Conversely, the reference voltage at comparator input 29 decreases with decreasing engine speed. At low engine speeds, below 3,000 rpm, the voltage at comparator input 29 is low enough that comparator output 52 will remain high, which in turn keeps FET 14 conductive, which in turn provides minimum voltage at node 16 during the initial timing interval, thus disabling knock detecting during initial engine acceleration.

It is recognized that various equivalents, alternatives and modifications are possible within the scope of the appended claims.

What is claimed is:

1. A knock detection circuit for an internal combustion engine, comprising:
    transducer means sensing audio signals indicative of engine combustion and occurring within a combustion chamber of the engine and converting said audio signals into a transducer output voltage including a portion representing background noise and a portion representing detonation;
    means for adjusting the amplitude of said transducer output voltage;
    means sampling said portion of said transducer output voltage representing background noise and controlling said adjusting means to decrease the amplitude of said transducer output voltage for increased sensed background noise and to increase the amplitude of said transducer output voltage for decreased sensed background noise;
    detonation threshold means responsive to a predetermined increase in the amplitude of said portion of said transducer output voltage representing detonation above the amplitude of said portion of said transducer output voltage representing background noise, and outputting a knock-detected signal;
    combination fail-safe and idle override means comprising means responsive to loss of said transducer output voltage to provide said knock-detected signal in a fail-safe mode, and responsive to engine speed below a given engine idle speed and preventing said fail-safe mode even if a low amplitude transducer output voltage, corresponding to low amplitude audio signals at idle, appears to be a loss of said transducer output voltage.

2. A knock detection circuit for an internal combustion engine, comprising:
    transducer means sensing audio signals indicative of engine combustion and occurring within a combustion chamber of the engine and converting said audio signals into a transducer output voltage including a portion representing background noise and a portion representing detonation;
    means for adjusting the amplitude of said transducer output voltage;
    means sampling said portion of said transducer output voltage representing background noise and controlling said adjusting means to decrease the amplitude of said transducer output voltage for increased sensed background noise and to increase the amplitude of said transducer output voltage for decreased sensed background noise;
    detonation threshold means responsive to a predetermined increase in the amplitude of said portion of said transducer output voltage representing detonation above the amplitude of said portion of said transducer output voltage representing background noise, and outputting a knock-detected signal;
    comparator means connected to said transducer means and comparing transducer output voltage against a reference voltage, and providing said knock detected signal when said transducer output voltage is below said reference voltage;
    means connected to said comparator means and responsive to engine speed to disable said comparator means from providing said knock-detected signal at engine speeds less than a given speed;
    wherein said means connected to said comparator means comprises timer means connected to the junction of said transducer means and said comparator means and responsive to ignition pulses to output timing pulses having a negative polarity for a given interval followed by a positive polarity interval until the next ignition pulse, such that at engine speeds below said given speed there is sufficient duration of said positive polarity intervals to maintain the voltage at the input to said comparator means above said reference voltage and disables said comparator means from providing said knock-detected signal regardless of a decrease in said transducer output voltage below said reference voltage, and such that at increased engine speed above said given speed the duration of said positive polarity intervals of said timing pulses become shorter because the next ignition pulse occurs sooner, and there is insufficient duration of said positive polarity intervals to maintain the voltage at the input to said comparator means above said reference voltage, such that said comparator means is controlled by said transducer output voltage and provides said knockdetected signal when said transducer means output voltage drops below said reference voltage.

3. A knock detection circuit for an interval combustion engine, comprising:
    transducer means sensing audio signals indicative of engine combustion and occurring within a combustion chamber of the engine and converting said audio signals into a transducer output voltage including a portion representing background noise and a portion representing detonation;
    transistor means connected to said transducer means and having a gain which affects the amplitude of said transducer output voltage;

comparator means having an input from said transducer means and having an output biasing said transistor means to control the gain of the latter to control said transducer output voltage inversely to sensed background noise;

detonation threshold means responsive to a predetermined increase in the amplitude of said portion of said transducer output voltage representing detonation above the amplitude of said portion of said transducer output voltage representing background noise, and outputting a knock-detected signal;

wherein said combustion is triggered by an ignition pulse, and comprising:

timer means responsive to said ignition pulse and enabling said comparator means only during a predetermined interval immediately following said ignition pulse during which detonation is unlikely to occur, such that said bias from said comparator means and said gain of said transistor means are adjusted substantially only during said interval;

second comparator means connected to said transducer means and comparing transducer output voltage against a reference voltage, and providing said knock-detected signal when said transducer output voltage is below said reference voltage.

4. The invention according to claim 3 comprising second timer means connected to said second comparator means and responsive to engine speed to disable said second comparator means from providing said knock-detected signal at engine speeds less than a given speed.

5. A knock detection circuit for an internal combustion engine, comprising:

transducer means sensing audio signals indicative of engine combustion and occurring within a combustion chamber of the engine and converting said audio signals into a transducer output voltage which is characterized, for each engine cycle, by one phase during which detonation is unlikely to occur and by another phase during which any detonation is likely to occur, said one phase representing background noise;

amplifier means controlling the amplitude of said transducer output voltage according to the gain of said amplifier means, and including automatic gain control means varying the gain of said amplifier means during said one phase inversely to the amplitude of said transducer output voltage corresponding to said audio signals;

detonation threshold means responsive to a predetermined increase in the amplitude of said transducer output voltage corresponding to detonation above the amplitude of said transducer output voltage corresponding to background noise, and outputting a knock-detected signal;

combination fail-safe and idle override means comprising means responsive to loss of said transducer output voltage to supply said knock-detected signal in a fail-safe mode, and responsive to engine speed below a given engine idle speed and preventing said fail-safe mode even if a low amplitude transducer output voltage, corresponding to low amplitude audio signals at idle, appears to be a loss of said transducer output voltage.

6. The invention according to claim 5 wherein said signal from said detonation threshold means and said signal from said combination fail-safe and idle override means are each supplied to a common output node, and comprising a first diode connected in series aiding relation from said detonation threshold means to said output node and passing said knockdetected signal from said detonation threshold means to said node and blocking passage of said knock-detected signal from said node to said detonation threshold means, and comprising a second diode connected in series aiding relation from said combination fail-safe and idle override means to said node and passing said knock-detected signal from said combination fail-safe and idle override means to said node and blocking passage of said knock-detected signal from said node to said combination fail-safe and idle override means.

7. A knock detection circuit for an internal combustion engine, comprising:

transducer means sensing audio signals indicative of engine combustion and occurring within a combustion chamber of the engine and converting said audio signals into a transducer output voltage which is characterized, for each engine cycle, by one phase during which detonation is unlikely to occur and by another phase during which any detonation is likely to occur, said one phase representing background noise;

amplifier means controlling the amplitude of said transducer output voltage according to the gain of said amplifier means, and including automatic gain control means varying the gain of said amplifier means during said one phase inversely to the amplitude of said transducer output voltage corresponding to said audio signals;

detonation threshold means responsive to a predetermined increase in the amplitude of said transducer output voltage corresponding to detonation above the amplitude of said transducer output voltage corresponding to background noise, and outputting a knock-detected signal;

comparator means connected to transducer means and comparing transducer output voltage against a reference voltage, and wherein said amplifier means comprises transistor means having a pair of main terminals connected in circuit with said transducer means and having a control terminal connected to the output of said comparator means to control conduction of said transistor means, such that said comparator means responds to an increase in transducer output voltage by increasing conduction of said transistor means to lower said transducer output voltage, and such that said comparator means responds to a decrease in transducer output voltage by decreasing conduction of said transistor means to raise said transducer output voltage, and wherein said detonation threshold means is connected to the junction of said transducer means and said transistor means;

said comparator means has a first input connected to said junction of said transducer means and said transistor means, and a second input supplied by said reference voltage;

said first input of said comparator means is connected to said junction of said transducer means and said transistor means through second transistor means, said second transistor means having a first main terminal connected to said junction of said transducer means and said first mentioned transistor means, said second transistor means having a second main terminal connected to said first input of said comparator means, said second transistor means having a control terminal for controlling conduction of said second transistor means, and comprising timer means connected to said control terminal of said second transistor means and responsive to an ignition pulse to render said second transistor means conductive for a timing interval providing said one phase, such that said transducer output voltage is applied to said first input of said comparator means during said timing interval.

8. The invention according to claim 7 wherein said timer means renders said second transistor means nonconductive at the end of said timing interval to block application of said transducer output voltage to said first input of said comparator means for a second interval providing said other phase, and comprising capacitor means maintaining said first mentioned transistor means conductive at the beginning of said second interval.

9. The invention according to claim 8 wherein said capacitor means is connected to a node between said comparator means and said first transistor means and maintains a relatively smooth DC bias on said first transistor means at the end of said first interval to maintain the gain of said first transistor means and said transducer output voltage until any detonation or until the next ignition pulse, whichever occurs first.

10. The invention according to claim 8 wherein said capacitor means is connected to an input of said comparator means and maintains the state thereof at the end of said first interval.

11. The invention according to claim 8 wherein said capacitor means comprises:
a first capacitor connected to a node between said comparator means and said first transistor means for maintaining a relatively smooth DC bias on said first transistor means at the end of said first interval to maintain said first transistor means conductive; and
a second capacitor connected to an input of said comparator means for maintaining the state thereof at the end of said first interval to in turn maintain said first transistor means conductive.

12. A knock detection circuit for an internal combustion engine, comprising:
transducer means sensing audio signals indicative of engine combustion and occurring within a combustion chamber of the engine and converting said audio signals into a transducer output voltage which is characterized, for each engine cycle, by one phase during which detonation is unlikely to occur and by another phase during which any detonation is likely to occur, said one phase representing background noise;
amplifier means controlling the amplitude of said transducer output voltage according to the gain of said amplifier means, and including automatic gain control means varying the gain of said amplifier means during said one phase inversely to the amplitude of said transducer output voltage corresponding to said audio signals;
detonation threshold means responsive to a predetermined increase in the amplitude of said transducer output voltage corresponding to detonation above the amplitude of said transducer output voltage corresponding to background noise, and outputting a knock-detected signal;
comparator means connected to said transducer means and comparing transducer output voltage against a reference voltage, and providing a knock-detected signal when said transducer output voltage is below said reference voltage;
means connected to said comparator means and responsive to engine speed to disable said comparator means from providing said knock-detected signal at engine speeds less than a given speed;
wherein said means connected to said comparator means comprises timer means connected to the junction of said transducer means and said comparator means and responsive to ignition pulses to output timing pulses having a negative polarity for a given interval followed by a positive polarity interval until the next ignition pulse, such that at engine speeds below said given speed there is sufficient duration of said positive polarity intervals to maintain the voltage at the input to said comparator means above said reference voltage and disable said comparator means from providing said knock-detected signal regardless of a decrease in said transducer output voltage below said reference voltage, and such that at increased engine speed above said given speed the duration of said positive polarity intervals of said timing pulses become shorter because the next ignition pulse occurs sooner, and there is insufficient duration of said positive polarity intervals to maintain the voltage at the input to said comparator means above said reference voltage, such that said comparator means is controlled by said transducer output voltage and provides said knockdetected signal when said transducer output voltage drops below said reference voltage.

13. A knock detection circuit for an internal combustion engine, comprising:
transducer means sensing audio signals indicative of engine combustion and occurring within a combustion chamber of the engine and converting said audio signals into a transducer output voltage which is characterized, for each engine cycle, by one phase during which detonation is unlikely to occur and by another phase during which any detonation is likely to occur, said one phase representing background noise;
amplifier means controlling the amplitude of said transducer output voltage according to the gain of said amplifier means, and including automatic gain control means varying the gain of said amplifier means during said one phase inversely to the amplitude of said transducer output voltage corresponding to said audio signals;
detonation threshold means responsive to a predetermined increase in the amplitude of said transducer output voltage corresponding to detonation above the amplitude of said transducer output voltage corresponding to background noise, and outputting a knock-detected signal;
comparator means connected to said transducer means and comparing transducer output voltage against a reference voltage, and wherein said amplifier means comprises transistor means having a pair of main terminals connected in circuit with said transducer means and having a control terminal connected to the output of said comparator means to control conduction of said transistor means, such that said comparator means responds to an increase in transducer output voltage by increasing conduction of said transistor means to lower said transducer output voltage, and such that said comparator means responds to a decrease in transducer output voltage by decreasing conduction of said transistor means to raise said transducer output voltage, and wherein said detonation threshold means is connected to the junction of said transducer means and said transistor means;

and comprising timer means responsive to ignition pulses and outputting timing pulses providing said reference voltage, said timing pulses having a positive polarity for a given interval followed by a negative polarity interval until the next ignition pulse, such that said reference voltage increases with increasing engine speed.

14. The invention according to claim 13 wherein said reference voltage decreases with decreasing engine speed, and such that at low engine speeds below a given speed, said reference voltage is low enough that said comparator output remains high which keeps said transistor means conductive which in turn provides minimum transducer output voltage.

15. A knock detection circuit for an internal combustion engine, comprising:

transducer means sensing audio signals indicative of engine combustion and occurring within a combustion chamber of the engine and converting said audio signals into a transducer output voltage which is characterized, for each engine cycle, by one phase during which detonation is unlikely to occur and by another phase during which any detonation is likely to occur, said one phase representing background noise;

amplifier means controlling the amplitude of said transducer output voltage according to the gain of said amplifier means, and including automatic gain control means varying the gain of said amplifier means during said one phase inversely to the amplitude of said transducer output voltage corresponding to said audio signals;

detonation threshold means responsive to a predetermined increase in the amplitude of said transducer output voltage corresponding to detonation above the amplitude of said transducer output voltage corresponding to background noise, and outputting a knock-detected signal;

comparator means connected to said transducer means and comparing transducer output voltage against a reference voltage, and wherein said amplifier means comprises transistor means having a pair of main terminals connected in circuit with said transducer means and having a control terminal connected to the output of said comparator means to control conduction of said transistor means, such that said comparator means responds to an increase in transducer output voltage by increasing conduction of said transistor means to lower said transducer output voltage, and such that said comparator means responds to a decrease in transducer output voltage by decreasing conduction of said transistor means to raise said transducer output voltage, and wherein said detonation threshold means is connected to the junction of said transducer means and said transistor means;

wherein said detonation threshold means comprises operational amplifier means having an input connected to a capacitor charged by voltage from said junction of said transducer means and said transistor means.

16. The invention according to claim 15 wherein said capacitor at said input of said operational amplifer means is also charged by the output of said comparator means to provide a higher charge on said capacitor means for higher sensed background noise.

* * * * *